(12) United States Patent
Xu

(10) Patent No.: US 11,492,416 B2
(45) Date of Patent: Nov. 8, 2022

(54) ACTIVATION OF (NA⁺+K⁺)-ATPASE INHIBITS PLATELET AGGREGATION AND PREVENTS THROMBOSIS

(71) Applicant: Kai Yuan Xu, Cockeysville, MD (US)

(72) Inventor: Kai Yuan Xu, Cockeysville, MD (US)

(*) Notice: Subject to any disclaimer, the term of this patent is extended or adjusted under 35 U.S.C. 154(b) by 85 days.

(21) Appl. No.: 16/409,841

(22) Filed: May 12, 2019

(65) Prior Publication Data

US 2019/0263933 A1    Aug. 29, 2019

Related U.S. Application Data

(63) Continuation-in-part of application No. 15/232,773, filed on Aug. 9, 2016, now Pat. No. 10,287,361.

(51) Int. Cl.
| | | |
|---|---|---|
| *A61K 38/36* | (2006.01) |
| *A61P 7/02* | (2006.01) |
| *C07K 14/745* | (2006.01) |
| *A61K 38/16* | (2006.01) |
| *C07K 16/00* | (2006.01) |
| *A61K 39/00* | (2006.01) |
| *A61K 39/395* | (2006.01) |
| *C07K 16/40* | (2006.01) |
| *C12N 9/14* | (2006.01) |

(52) U.S. Cl.
CPC ............. *C07K 16/40* (2013.01); *A61K 38/16* (2013.01); *A61K 39/0005* (2013.01); *A61K 39/395* (2013.01); *A61K 39/3955* (2013.01); *A61P 7/02* (2018.01); *C07K 16/00* (2013.01); *C12N 9/14* (2013.01); *A61K 2039/505* (2013.01); *C07K 2317/34* (2013.01); *C07K 2317/76* (2013.01)

(58) Field of Classification Search
None
See application file for complete search history.

*Primary Examiner* — Thea D' Ambrosio

(57) ABSTRACT

Methods of inhibiting platelet activation and aggregation using antibodies or peptide vaccines having binding specificity for the α subunit of the (Na⁺+K⁺)-ATPase are provided, along with methods for inhibiting or preventing or treating thrombosis in a subject using such antibodies.

8 Claims, 5 Drawing Sheets

Specification includes a Sequence Listing.

ACTIVATION OF (NA$^+$+K$^+$)-ATPASE INHIBITS PLATELET AGGREGATION AND PREVENTS THROMBOSIS

This application is a Continuation-In-Part of prior application Ser. No. 15/232,773 filed on Aug. 9, 2016 and U.S. Pat. No. 10,287,361, both of which are hereby incorporated by reference herein in their entirety.

TECHNICAL FIELD

The invention relates to methods for inhibiting platelet aggregation and to methods for inhibiting and/or preventing/treating thrombosis using antibodies (including both endogenous and exogenous) that bind the alpha (α) subunit of the (Na$^+$+K$^+$)-ATPase (NKA) and increase NKA activity. Antibody capable of increasing NKA activity (activation of NKA) is called NKA activator antibody.

BACKGROUND OF INVENTION

Thrombosis is the pathological formation of a blood clot (thrombus) which comprises aggregated platelets and a mesh of cross-linked fibrin protein within a blood vessel. A thrombus can restrict blood flow to downstream tissues supplied by the blocked blood vessel. Thrombosis thus deprives the downstream tissue of oxygen and nutrients, and can cause infarction and tissue death. Thrombosis can cause myocardial infarction in the heart when the thrombosis involves a coronary artery supplying the heart, can cause a stroke when the thrombosis involves a blood vessel in the brain, and can cause lung embolism when thrombosis lodges in lungs. Depending upon the location of a blot clot within the circulatory system, thrombosis can also cause disease in the kidney, liver, extremities, and other bodily locations.

Antiplatelet medications are most effective at preventing arterial blood clots which are composed largely of platelets. Antiplatelet medications are administered to patients who have coronary artery disease, angina, heart failure, heart valve disease, or at risk for coronary artery disease or stroke, to help prevent a heart attack or stroke.

Thrombosis remains the world's largest single cause of mortality, despite the fact that medication has been available for over 50 years to treat and prevent the condition. Clearly, new treatments for thrombosis are needed.

BRIEF SUMMARY OF INVENTION (Na$^+$+K$^+$)-ATPase (NKA; the sodium pump) is a transmembrane enzyme responsible for the active reciprocal transport of Na$^+$ and K$^+$ ions across the plasma membrane of all animal cells. NKA comprises two basic subunits: the α subunit and the β subunit. The larger α subunit is the functional subunit, which catalyzes the hydrolysis of ATP for active transport of Na$^+$ and K$^+$ ions across the plasma membrane; the smaller β subunit does not participate in the catalytic process of the enzyme, but instead acts as a specific chaperone that assists the biogenesis and correct membrane insertion of newly synthesized NKA. The α subunit of NKA has three isoforms including α1, α2 and α3. The β subunit of NKA also has three isoforms including β1, β2 and β3.

The present invention is based on the surprising discovery that activation of NKA can inhibit platelet aggregation using NKA activator antibodies that bind the α subunit of NKA of platelets and increase NKA activity. NKA activator antibodies with α subunit binding specificity can be used to inhibit platelet aggregation, and inhibit or prevent/treat thrombosis in a subject. Such NKA activator antibodies thus form the basis of methods of treating or preventing blood clots associated with diseases such as stroke, myocardial infarction, lung embolism, deep vein thrombosis, and generally any venous or arterial thrombosis resulting from platelet aggregation and resulting in patient morbidity or mortality.

Examples of NKA activator antibodies having α subunit binding specificity that can be used in the methods of the present invention include, but are not limited to, SSA78 (also referred as Jianye 2), SSA401 (also referred as KX-2), and SSA412 (also referred as KX-1), polyclonal, monoclonal, humanized and human versions thereof, and fragments thereof. These antibodies are capable of increasing NKA enzymatic activity (activation of NKA), which are described in Patent Publication No. PCT/US2006/012912, U.S. Ser. No. 11/910,943, and U.S. Pat. No. 9,409,949, 9,416,159, 8,435,519, and 10,287,361, which are herein incorporated by reference in their entirety for all purposes.

In a first aspect, the invention thus provides methods for inhibiting platelet activation comprising contacting platelets with an antibody having binding specificity for the α subunit of NKA. Exemplary antibodies that may be used in these methods include, but are not limited to, (i) antibodies having binding specificity for the α subunit of NKA, (ii) antibodies having binding specificity for one or more of the peptides represented by SEQ ID NOs:1-5, (iii) NKA activator antibodies in a humanized or human versions thereof, or a fragment or derivative thereof, and (iv) antigens of SEQ ID NOs: 1-5 to generating endogenous NKA activator antibody, in a human or polyclonal versions thereof, or a fragment or derivative thereof. The method may be conducted in vitro or in vivo. The method may also be conducted in blood ex vivo.

In a second aspect, the invention provides methods for inhibiting platelet aggregation comprising contacting platelets with an antibody having binding specificity for the α subunit of NKA. Exemplary antibodies that may be used in these methods include, but are not limited to, (i) antibodies having binding specificity for the α subunit of NKA, (ii) antibodies having binding specificity for one or more of the peptides represented by SEQ ID NOs:1-5, (iii) NKA activator antibodies in a humanized or human versions thereof, or a fragment or derivative thereof, and (iv) using SEQ ID NOs: 1-5 peptide antigen to generate endogenous NKA activator antibodies, in human or polyclonal versions thereof, or a fragment or derivative thereof. The method may be conducted in vitro or in vivo. The method may also be conducted in blood ex vivo.

In a third aspect, the invention provides methods for inhibiting platelet aggregation in a subject comprising administering an effective amount of an antibody having binding specificity for the a subunit of NKA to a subject in need thereof. Exemplary antibodies that may be used in these methods include, but are not limited to, (i) antibodies having binding specificity for the α subunit of NKA, (ii) antibodies having binding specificity for one or more of the peptides represented by SEQ ID NOs:1-5, (iii) NKA activator antibodies in a humanized or human versions thereof, or a fragment or derivative thereof, and (iv) using SEQ ID NOs: 1-5 peptide antigen to generate endogenous NKA activator antibodies, in human or polyclonal versions thereof, or a fragment or derivative thereof. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a fourth aspect, the invention provides methods for inhibiting thrombosis in a subject comprising administering an effective amount of an antibody having binding specificity for the a subunit of NKA to a subject in need thereof. Exemplary antibodies that may be used in these methods include, but are not limited to, (i) antibodies having binding specificity for the a subunit of NKA, (ii) antibodies having binding specificity for one or more of the peptides represented by SEQ ID NOs:1-5, (iii) NKA activator antibodies in a humanized or human versions thereof, or a fragment or derivative thereof, and (iv) using SEQ ID NOs: 1-5 peptide antigen to generate endogenous NKA activator antibodies, in human or polyclonal versions thereof, or a fragment or derivative thereof. The subject may one that is at greater risk than the general population for thrombosis. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a fifth aspect, the invention provides methods for treating thrombosis in a subject comprising administering an effective amount of an antibody having binding specificity for the α subunit of NKA to a subject in need thereof. Exemplary antibodies that may be used in these methods include, but are not limited to, (i) antibodies having binding specificity for the α subunit of NKA, (ii) antibodies having binding specificity for one or more of the peptides represented by SEQ ID NOs:1-5, (iii) NKA activator antibodies in a humanized or human versions thereof, or a fragment or derivative thereof, and (iv) using SEQ ID NOs: 1-5 peptide antigen to generate endogenous NKA activator antibodies, in human or polyclonal versions thereof, or a fragment or derivative thereof. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a sixth aspect, the invention provides methods for preventing thrombosis in a subject comprising administering an effective amount of an antibody having binding specificity for the α subunit of NKA to a subject in need thereof. Exemplary antibodies that may be used in these methods include, but are not limited to, (i) antibodies having binding specificity for the α subunit of NKA, (ii) antibodies having binding specificity for one or more of the peptides represented by SEQ ID NOs:1-5, (iii) NKA activator antibodies in a humanized or human versions thereof, or a fragment or derivative thereof, and (iv) using SEQ ID NOs: 1-5 peptide antigen to generate endogenous NKA activator antibodies, in human or polyclonal versions thereof, or a fragment or derivative thereof. The subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

In a seventh aspect, the invention provides methods for treating a disease of disregulated platelet aggregation in a subject comprising administering an effective amount of an antibody having binding specificity for the α subunit of NKA to a subject in need thereof. Exemplary antibodies that may be used in these methods include, but are not limited to, (i) antibodies having binding specificity for the α subunit of NKA, (ii) antibodies having binding specificity for one or more of the peptides represented by SEQ ID NOs:1-5, (iii) NKA activator antibodies in a humanized or human versions thereof, or a fragment or derivative thereof, and (iv) using SEQ ID NOs: 1-5 peptide antigen to generate endogenous NKA activator antibodies, in human or polyclonal versions thereof, or a fragment or derivative thereof. Exemplary diseases of dysregulated platelet aggregation include, but are not limited to, hypercoagulability, essential thrombocythemia, reactive thrombocytosis, thrombocytopenia, von Willebrand disease, hereditary intrinsic platelet disorders (e.g., Bernard-Soulier syndrome, May-Hegglin anomaly, Chédiak-Higashi syndrome), and acquired disorders of platelet function (e.g., myeloproliferative and myelodysplastic disorders, uremia, macroglobulinemia, multiple myeloma, cirrhosis).

In each of these aspects, the antibody may be in a pharmaceutical formulation comprising the antibody and a pharmaceutically acceptable carrier.

The foregoing has outlined rather broadly the features and technical advantages of the present invention in order that the detailed description of the invention that follows may be better understood. Additional features and advantages of the invention will be described herein, which form the subject matter of the claims of the invention.

DETAILED DESCRIPTION OF THE INVENTION

Figure 1:
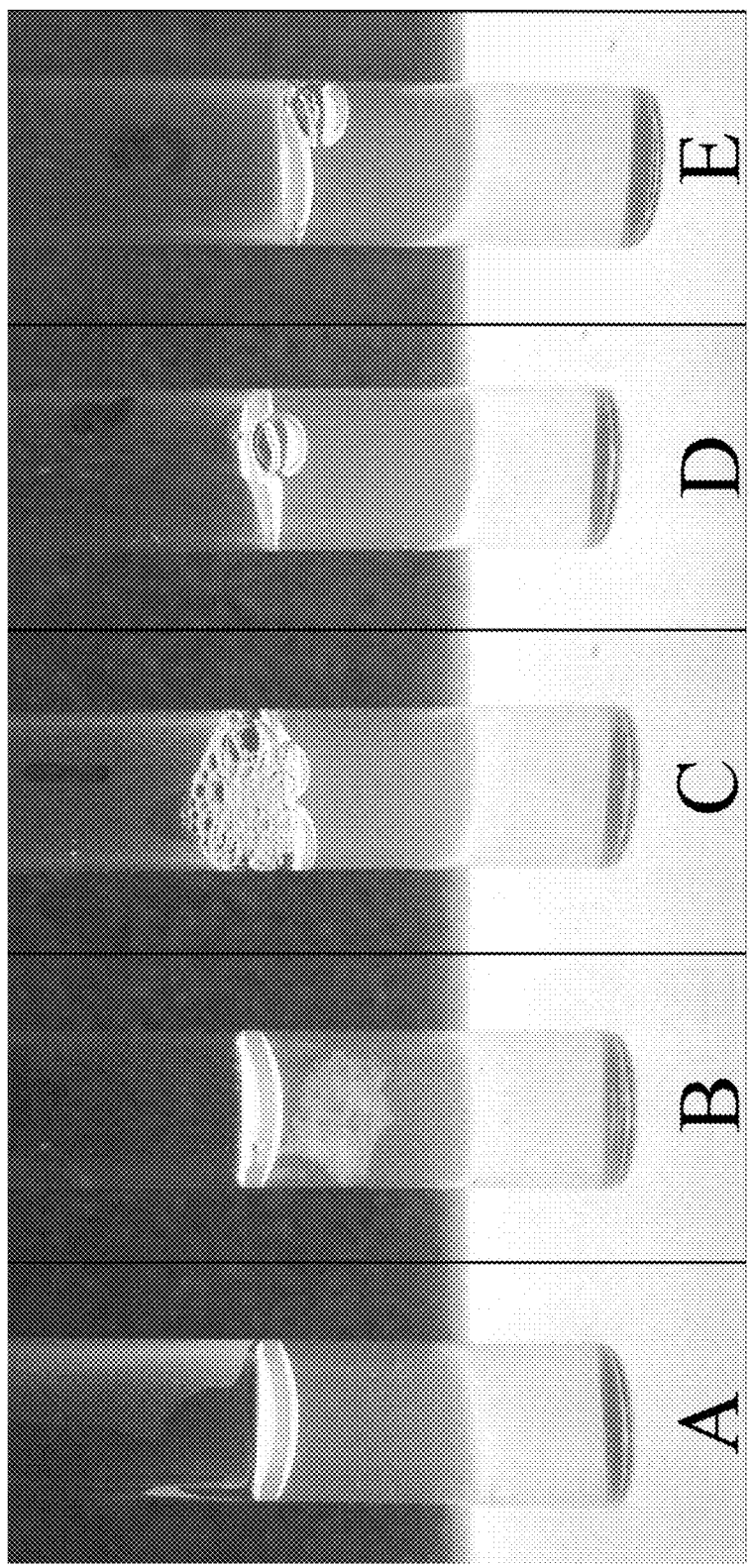
FIG. 1. NKA activator antibodies SSA78, SSA401 and SSA412 prevent and inhibit collagen-induced platelet aggregation. Platelet-rich human blood plasma (tube A) is a turbid liquid. Upon addition of collagen (1 µg/ml), platelets are activated leading to aggregation (tube B). In the presence of NKA activator SSA78 (tube C), SSA401 (tube D), or SSA412 (tube E) prior to add collagen (1 µg/ml), NKA activators SSA78, SSA401, and SSA412 (0.2 µM each) prevent/inhibit platelet activation and aggregation in tubes C, D, and E, respectively.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As outlined in a general manner above, the present invention is based on the surprising discovery that platelet aggregation can be inhibited using antibodies that bind the α subunit of NKA of platelets. Thus, the α subunit binding-antibodies can be used to inhibit platelet activation and aggregation, whether in vitro or in vivo, to inhibit, treat, and prevent thrombosis in a subject, and to treat a disease of dysregulated platelet aggregation in a subject. The antibodies also form the basis of methods of treating or preventing blood clots associated with diseases such as stroke, myocardial infarction, deep vein thrombosis, and generally any venous or arterial thrombosis resulting from platelet aggregation and resulting in patient morbidity or mortality.

Antibodies

The skilled artisan will understand that the particular attributes of the antibodies that may be used in the methods of the present invention are only confined by (i) the ability to bind with specificity to the α subunit of NKA, and (ii) the ability to inhibit platelet aggregation.

As described in PCT/US2006/012912 (U.S. Pat. No. 9,409,949, 9,416,159, 8,435,519, 10,287,361), five antibodies have been prepared that specifically bind the α subunit of NKA, namely antibody SSA95 (also referred as Jianye 1 antibody), SSA97 (also referred as Zulan antibody), SSA78 (also referred as Jianye 2 antibody), SSA401 (also referred as KX-2 antibody), and SSA412 (also referred as KX-1 antibody). As shown in the Examples below, these antibodies inhibit platelet aggregation and may be used in the methods of the present invention. Antibody SSA95 binds to amino acids KRQPRNPKTDKLVNE (SEQ ID NO:1), SSA97 binds to amino acids VPAISLAYEQAESD (SEQ ID NO:2), SSA78 binds to amino acids RSATEEEPPNDD (SEQ ID NO:3), SSA401 binds to amino acids HLL-GIRETWDDRWIN (SEQ ID NO:4), and SSA412 binds to amino acids DVEDSYGQQWTYEQR (SEQ ID NO:5). The invention therefore provides the use of NKA activator antibodies SSA95, SSA97, SSA78, SSA401, and antibody SSA412 in the methods disclosed herein.

The invention also provides the use of antibodies that specifically bind an epitope of the α subunit of NKA comprising the amino acid sequence KRQPRNPKTDKLVNE (SEQ ID NO:1), VPAISLAYEQAESD (SEQ ID NO:2), RSATEEEPPNDD (SEQ ID NO:3), HLLGIRETWDDRWIN (SEQ ID NO:4), and DVEDSYGQQWTYEQR (SEQ ID NO:5), or any combination thereof.

The invention further provides for the use of antibodies having binding specificity for an epitope of α subunit of NKA comprising the amino acid SEQ ID NOs: 1-5. Antibody SSA95 binds to amino acids KRQPRNPKTDKLVNE (SEQ ID NO:1), SSA97 binds to amino acids VPAISLAYEQAESD (SEQ ID NO:2), SSA78 binds to amino acids RSATEEEPPNDD (SEQ ID NO:3), SSA401 binds to amino acids HLLGIRETWDDRWIN (SEQ ID NO:4), and SSA412 binds to amino acids DVEDSYGQQWTYEQR (SEQ ID NO:5).

The invention further provides for the use of antibodies having binding specificity for variants of each of the peptides of SEQ ID NOs:1-5, the variants having 8 or fewer, 5 or fewer, 4 or fewer, 3 or fewer, 2 or fewer, or 1 amino acid change in comparison to the peptides of SEQ ID NOs:1-5. The changes are each individually selected from insertions, deletions and substitutions. The substitutions may be conservative or non-conservative amino acid substitutions. Each of the variant peptides maintains the ability to induce production of antibodies that specifically bind the α subunit of NKA and that have the ability to inhibit platelet aggregation.

In addition, the invention provides for the use of antibodies having binding specificity for other epitopes of α subunit of NKA, with those antibodies having binding specificity for other epitopes of the α subunit of NKA being of particular note.

The antibodies used in the methods of the present invention and defined above may be polyclonal, monoclonal, humanized or chimeric antibodies, and the antibodies may be in the form of an antiserum comprising the antibodies. The antibodies may be of any class, such as IgG1, IgG2, IgG3, IgG4, IgM, IgA1, IgA2, IgD or IgE. The antibodies may be isolated antibodies, purified antibodies, exogenous antibodies, endogenous antibodies, or a combination thereof.

The antibodies may also be antibody fragments of less than the entire antibody, including, but not limited to, single chain antibodies, F(ab')$_2$ fragments, Fab fragments, and fragments produced by an Fab expression library, and derivatives of the antibodies and fragments defined herein, with the only limitation being that the antibody fragments and derivatives retain the ability to bind the α subunit and aggregate platelets. It will thus be clear to the skilled artisan that all references to "antibodies" herein include both full-size antibodies as well as antibody fragments, as defined herein.

The antibodies may be produced in any species of animal, though preferably from a mammal such as a human, simian, mouse, rat, rabbit, guinea pig, horse, cow, sheep, goat, pig, dog or cat. For example, the antibodies can be human antibodies or humanized antibodies, or any antibody preparation suitable for administration to a human. For the production of the antibodies, the selected species of animal can be immunized by injection with one or more of the peptides or variants discussed herein. The peptides and variants may be administered in conjunction with one or more pharmaceutically acceptable adjuvants to increase the immunological response. Suitable adjuvants include, but are not limited to, Freund's Complete and Incomplete Adjuvant, Titermax, Oil in Water Adjuvants, as well as Aluminum compounds where antigens, normally peptides, are physically precipitated with hydrated insoluble salts of aluminum hydroxide or aluminum phosphate. Other adjuvants include liposome-type adjuvants comprising spheres having phospholipid bilayers that form an aqueous compartment containing the peptide and protect it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from E. coli. Immunomodulation through the use of anti-IL-17, anti IFN-γ, anti-IL-12, IL-2, IL-10, or IL-4 may also be used to promote a strong Th2 or antibody mediated response to the immunogenic formulation.

Means for preparing antibodies are very well known in the art. The antibodies of the invention can be prepared using any known technique that provides for the production of antibody molecules. Suitable techniques include, but are not limited to, the hybridoma technique originally described by Koehler and Milstein (Nature 256:495-497 (1975)), the human B-cell hybridoma technique (Kosbor et al., Immunol Today 4:72 (1983); Cote et al., Proc Natl. Acad. Sci 80:2026-2030 (1983)), and the EBV-hybridoma technique (Cole et al., Monoclonal Antibodies and Cancer Therapy, Alan R. Liss Inc, New York, N.Y., pp 77-96 (1985)). Each of these publications is herein incorporated by reference in its entirety. Additionally, antibodies can be produced by inducing in vivo production in the lymphocyte population or by screening recombinant immunoglobulin libraries or panels of highly specific binding reagents as disclosed in Orlandi et al., *Proc Natl. Acad. Sci. USA* 86: 3833-3837 (1989), and in Winter G. and Milstein C., *Nature* 349:293-299 (1991), both of which is herein incorporated by reference in its entirety.

Humanized antibodies are those where a human antibody has been engineered to contain non-human complementarity-determining regions (CDRs) derived from an antibody produced in a non-human host against a selected antigen. Means for producing humanized antibodies are well-known in the art and include Vaswani S K, and Hamilton R G, *Ann Allergy Asthma Immunol.* 81(2):105-15 (1998) and Kashmiri S V et al., *Methods* 36 (1):25-34 (2005), each of which is herein incorporated by reference in its entirety.

Human antibodies are those where an antibody produced in a non-human host against a selected antigen. Means for producing human antibodies are well-known in the art and include Bruggemann M et al., *Arch Immunol Ther Exp (Warsz).* 63(2):101-108 (2014), Pruzina S et al., *Protein Eng Des Sel.* 24 (10):791-799 (2011), and Smith K et al., *Nature.* 4:372-384 (2009), each of which is herein incorporated by reference in its entirety.

Chimeric antibodies are those where an antigen binding region (e.g., F(ab')$_2$ or hypervariable region) of a non-human antibody is transferred into the framework of a human antibody by recombinant DNA techniques. Techniques developed for the production of such antibodies include the splicing of mouse antibody genes to human antibody genes to obtain a molecule with appropriate antigen specificity and biological activity. Such techniques are also well known and include: Morrison et al., *Proc Natl. Acad. Sci* 81:6851-6855 (1984); Neuberger et al., *Nature* 312:604-608(1984); Takeda et al., *Nature* 314:452-454(1985), each of which is herein incorporated by reference in its entirety.

Techniques for the production of single chain antibodies are described in U.S. Pat. No. 4,946,778, incorporated herein by reference in its entirety.

Antibody fragments such as F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse W. D. et al., Science 256:1275-1281 (1989), herein incorporated by reference in its entirety).

The invention provides for the use of pharmaceutical formulations comprising one or more of the antibodies of the invention and a pharmaceutically acceptable carrier. Such formulations may be administered to a subject when practicing the methods of the present invention. Suitable examples of carriers are well known to those skilled in the art and include water, water-for-injection, saline, buffered saline, dextrose, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. The formulations may further comprise stabilizing agents, buffers, antioxidants and preservatives, tonicity agents, bulking agents, emulsifiers, suspending or viscosity agents, inert diluents, fillers, and combinations thereof.

The identity of the carrier(s) will also depend on the means used to administer pharmaceutical formulations comprising antibodies to a subject. For example, pharmaceutical formulations for intramuscular preparations can be prepared where the carrier is water-for-injection, 0.9% saline, or 5% glucose solution. Pharmaceutical formulations may also be prepared as liquid or powdered atomized dispersions for delivery by inhalation. Such dispersion typically contain carriers common for atomized or aerosolized dispersions, such as buffered saline and/or other compounds well known to those of skill in the art. The delivery of the pharmaceutical formulations via inhalation has the effect of rapidly dispersing the vaccine formulation to a large area of mucosal tissues as well as quick absorption by the blood for circulation. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

Additionally, the pharmaceutical formulations may also be administered in a liquid form. The liquid can be for oral dosage, for ophthalmic or nasal dosage as drops, or for use as an enema or douche. When the pharmaceutical formulation is formulated as a liquid, the liquid can be either a solution or a suspension of the pharmaceutical formulation. There is a variety of suitable formulations for the solution or suspension of the pharmaceutical formulations that are well known to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents.

Peptide Vaccine

The skilled artisan will understand that the particular attributes of the peptide vaccines that may be used in the methods of the present invention are only confined by (i) the ability to generate specific antibodies that bind to specific epitopes of the α subunit of NKA, which are represented by SEQ ID NOS:1-5 or their derivatives, and (ii) the antibodies have the ability to inhibit platelet activation and aggregation.

As described in PCT/US2006/012912 (U.S. Pat. Nos. 9,409,949, 9,416,159, 8,435,519, 10,287,361,), five synthetic peptide vaccine KRQPRNPKTDKLVNE (SEQ ID NO:1), VPAISLAYEQAESD (SEQ ID NO: 2), RSATEEEPPNDD (SEQ ID NO:3), HLLGIRETWDDRWIN (SEQ ID NO: 4), and DVEDSYGQQWTYEQR (SEQ ID NO:5) were used to generate five antibodies that specifically bind the α subunit of NKA, namely antibody SSA95 (also referred as Jianye 1 antibody), SSA97 (also referred as Zulan antibody), SSA78 (also referred as Jianye 2 antibody), SSA401 (also referred as KX-2 antibody), and SSA412 (also referred as KX-1 antibody), As shown in the Examples below, these antibodies inhibit platelet aggregation and may be used in the methods of the present invention. Antibody SSA95 binds to amino acids KRQPRNPKTDKLVNE (SEQ ID NO:1), SSA97 binds to amino acids VPAISLAYEQAESD (SEQ ID NO:2), SSA78 binds to amino acids RSATEEEPPNDD (SEQ ID NO:3), SSA401 binds to amino acids HLLGIRETWDDRWIN (SEQ ID NO:4), and SSA412 binds to amino acids DVEDSYGQQWTYEQR (SEQ ID NO:5). The invention therefore provides the use of NKA peptide vaccines in the methods disclosed herein.

The invention also includes inhibiting platelet activation, aggregation, and thrombosis without causing bleeding by administering a peptide vaccine that includes one or more peptides selected from a group of peptides having the amino acid sequences KRQPRNPKTDKLVNE (SEQ ID NO:1), VPAISLAYEQAESD (SEQ ID NO:2), RSATEEEPPNDD (SEQ ID NO:3), HLLGIRETWDDRWIN (SEQ ID NO:4), DVEDSYGQQWTYEQR (SEQ ID NO:5), and variants or derivatives or fragments thereof. These peptides represent antigenic determinants or epitopes on α subunit of NKA. The peptide vaccines stimulate the host immune system to generate antibodies against the respective one or more peptide epitopes. Methods of using peptide antigen for making, isolating and purifying NKA activity-increasing antibodies and the above-identified peptide antigenic determinants are described in U.S. Patent Applications 20040057956 and 20030228315, the entire contents of which are hereby incorporated by reference as if fully set forth herein.

Peptide derivative or variants comprises the addition, substitution, deletion, insertion, or combination of one or more amino acids of SEQ ID NOs:1-5. Peptide vaccine derivatives or variants are described in U.S. Pat. Nos. 8,334,259, 7,041,442, 7,041,570, 7,361,731, 8,124,054, 8,815,266, 8,877,716, 9,328,143, 9,556,225, 10,047,122, 10,112,978, 9,956,275, 9,085,634, 8,03,435,3, 5,693,325, 5,484,592, and in Thomas W A, Biochem Soc Trans 14(2): 383-387(1986), D'Argenio D A, et al., J Bacteriol 181(20): 6478-6487(1999), the entire contents of which are hereby incorporated by reference as if fully set forth herein.

Methods for Inhibiting Platelet Aggregation As indicated above, the present invention includes methods for inhibiting platelet aggregation. This method comprising contacting platelets with an antibody having binding specificity for the α subunit of NKA. It will be apparent to the skilled artisan that this method can be practice in vitro, in vivo and ex vivo (e.g., in blood flowing through a heart bypass machine during surgery).

Any of the antibodies described herein, whether polyclonal or monoclonal, can be used in the method, as well as humanized or chimeric versions of the antibodies, and fragments of any of these. Exemplary antibodies that may be used in these methods include, but are not limited to, (i) antibodies having binding specificity for the α subunit of NKA, (ii) antibodies having binding specificity for one or more of the peptides represented by SEQ ID NOs:1-5, (iii) antibodies in polyclonal, monoclonal, humanized and human versions thereof, and (iv) antibodies in an exogenous or endogenous versions thereof.

Methods for Inhibiting Platelet Activation

The present invention includes methods for inhibiting platelet activation. This method comprising contacting platelets with an antibody having binding specificity for the α subunit of NKA. It will be apparent to the skilled artisan that this method can be practice in vitro, in vivo and ex vivo (e.g., in blood flowing through a heart bypass machine during surgery). Any of the antibodies described herein, whether polyclonal or monoclonal, can be used in the method, as well as humanized or chimeric versions of the antibodies, and fragments of any of these. Exemplary antibodies that may be used in these methods include, but are not limited to, (i) antibodies having binding specificity for the α subunit of NKA, (ii) antibodies having binding specificity for one or more of the peptides represented by SEQ ID NOs:1-5, (iii) antibodies polyclonal, monoclonal, humanized and human versions thereof, and (iv) antibodies in an exogenous or endogenous versions thereof.

Methods of Treatment

The invention also provides methods for treating or preventing particular diseases, disorders and conditions in a subject by inhibiting platelet aggregation.

The invention thus includes methods for inhibiting platelet aggregation in a subject comprising administering an effective amount of an antibody having binding specificity for the α subunit of NKA to a subject in need thereof. While the subject is not limited to one having a particular disease or condition, the subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, myocardial infarction, and post-surgical thrombotic complications arising from angioplasty and organ transplantation or other disease or condition wherein inhibition of platelet aggregation would be desirable or necessary.

The invention includes methods for inhibiting, treating or preventing thrombosis in a subject, where the method comprises administering an effective amount of an antibody having binding specificity for the α subunit of NKA to a subject in need thereof. While the subject is not limited to one having a particular disease or condition, the subject may be one that is characterized has having or at being at greater risk than the general population for one or more of the following diseases and conditions: venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, myocardial infarction, and post-surgical thrombotic complications arising from angioplasty and organ transplantation or other disease or condition wherein inhibition of platelet aggregation would be desirable or necessary.

The invention also includes methods for treating a disease of dysregulated platelet aggregation in a subject comprising administering an effective amount of an antibody having binding specificity for the α subunit of NKA to a subject in need thereof. Exemplary diseases of dysregulated platelet aggregation include, but are not limited to, hypercoagulability, essential thrombocythemia, reactive thrombocytosis, thrombocytopenia, von Willebrand disease, hereditary intrinsic platelet disorders (e.g., Bernard-Soulier syndrome, May-Hegglin anomaly, Chédiak-Higashi syndrome), and acquired disorders of platelet function (e.g., myeloproliferative and myelodysplastic disorders, uremia, macroglobulinemia, multiple myeloma, cirrhosis).

Any of the antibodies described herein, whether polyclonal or monoclonal, can be used in the method, as well as humanized or chimeric versions of the antibodies, and fragments and derivatives of any of these. Exemplary antibodies that may be used in these methods include, but are not limited to, (i) antibodies having binding specificity for the α subunit of NKA, including isoform of α subunit, (ii) antibodies having binding specificity for one or more of the peptides represented by SEQ ID NOs:1-5, (iii) antibodies in a polyclonal, monoclonal, humanized or human versions thereof, or a fragment or derivative thereof, and (iv) antibodies in an exogenous or endogenous versions thereof, or a fragment or derivative thereof. The antibody may be administered as a pharmaceutical formulation comprising the antibody and a pharmaceutically acceptable carrier.

As used herein, the terms "treat", "treating" and "treatment" have their ordinary and customary meanings, and include one or more of, ameliorating thrombosis or a disease of dysregulated platelet aggregation, ameliorating a symptom of thrombosis or a disease of dysregulated platelet aggregation, or decreasing in severity and/or frequency a symptom of thrombosis or a disease of dysregulated platelet aggregation. Treatment means ameliorating or decreasing by about 1% to about 100% versus a subject to which the antibody has not been administered. Preferably, the ameliorating or decreasing or inhibiting is about 100%, about 99%, about 98%, about 97%, about 96%, about 95%, about 90%, about 80%, about 70%, about 60%, about 50%, about 40%, about 30%, about 20%, about 10%, about 5% or about 1%. The treatment may begin prior to, concurrent with, or after the onset of clinical symptoms of thrombosis or a disease of dysregulated platelet aggregation. The results of the treatment may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "prevent", "preventing" and "prevention" have their ordinary and customary meanings, and include one or more of, stopping, averting, avoiding or blocking thrombosis, the occurrence of a symptom of thrombosis, the recurrence of a symptom of thrombosis, the development of thrombosis or the progression of thrombosis. Prevention means stopping by at least about 95% versus a subject to which the antibody has not been administered. Preferably, the stopping is about 100%, about 99%, about 98%, about 97%, about 96% or about 95%. The results of the prevention may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "inhibit", "inhibiting" and "inhibition" have their ordinary and customary meanings, and include one or more of, hindering, impeding, obstructing, deterring or restraining platelet aggregation or thrombosis, the occurrence of a symptom of platelet aggregation or thrombosis, the recurrence of a symptom of platelet aggregation or thrombosis, the development of platelet aggregation or thrombosis, or the progression of platelet aggregation or thrombosis. Inhibition means impeding by about 1% to about 100% versus a subject to which the antibody has not been administered. Preferably, the impeding is about 100%, about 99%, about 98%, about 97%, about 96%, about 95%, about 90%, about 80%, about 70%, about 60%, about 50%, about 40%, about 30%, about 20%, about 10%, about 5% or about 1%. The course of therapy may begin prior to, concurrent with, or after the onset of clinical symptoms of platelet aggregation or thrombosis. Thus, the subject may have platelet aggregation or thrombosis, or merely be susceptible to platelet aggregation or thrombosis. The results of the inhibition may be permanent or may continue for a period of days (such as 1, 2, 3, 4, 5, 6 or 7 days), weeks (such as 1, 2, 3 or 4 weeks) or months (such as 1, 2, 3, 4, 5, 6 or more months).

The antibodies and formulations may be administered to a subject using different schedules, depending on the particular aim or goal of the method; the age and size of the subject; and the general health of the subject, to name only a few factors to be considered. In general, the antibodies and formulations may be administered once, or twice, three times, four times, five times, six times or more, over a course of treatment, inhibition or prevention. The timing between each dose in a dosing schedule may range between days, weeks, months, or years, an includes administered once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more weeks. The same quantity of antibody may be administered in each dose of the dosing schedule, or the amounts in each dose may vary. The identity of the particular antibody may also vary or remain the same in each dose in a dosing schedule.

In each of the methods of the present invention, an "effective amount" of an antibody or a pharmaceutical formulation comprising an antibody is administered to a subject. The effective amount will vary between subjects. However, the effective amount is one that is sufficient to achieve the aim or goal of the method, whether inhibiting, treating or preventing. As an example, an effective amount of an antibody used in the methods of the invention is typically between about 0.1 µg to about 1000 µg of antibody per kg of body weight of the subject to which the antibody is administered. An effective amount also includes between about 1 µg to about 500 µg, between about 10 µg to about 200 µg, between about 1 µg to about 800 µg, between about 10 µg to about 800 µg, between about 1 µg to about 300 µg, and between about 10 µg to about 300 µg of antibody per kg of body weight of the subject.

Appropriate doses and dosing schedules can readily be determined by techniques well known to those of ordinary skill in the art without undue experimentation. Such a determination will be based, in part, on the tolerability and efficacy of a particular dose.

Administration of the antibody or formulation may be via any of the means commonly known in the art of antibody delivery. Such routes include intravenous, intraperitoneal, intramuscular, subcutaneous and intradermal routes of administration, as well as nasal application, by inhalation, ophthalmically, orally, rectally, vaginally, or by any other mode that results in the antibody or formulation contacting mucosal tissues.

The term "subject" is intended to mean an animal, such birds or mammals, including humans and animals of veterinary or agricultural importance, such as dogs, cats, horses, sheep, goats, and cattle.

A kit comprising the necessary components for practicing the methods of the invention, including an antibody or a pharmaceutical formulation comprising an antibody, and instructions for its use is also within the purview of the present invention.

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

EXAMPLES

Inhibition of ADP-induced Platelet Activation and Aggregation

Materials: ZEISS Axioskop microscope, Micro cover glass, Microscope slides, 1 mM ADP, human blood, and isolated human platelets. Method-1: Preparation of platelet-rich plasma (PRP): Human blood was collected from a healthy volunteer who was not on any medications. PRP was prepared by centrifuging blood at 100 g for 20 min at room temperature (with no brake applied) using a Sonvall Legend X1R centrifuge (Thermo Scienfific). After the spin, three distinct layers were observed. The top straw-colored layer was used as PRP. Method-2: Detection of collagen induced platelet aggregation: Fresh-made blood plasma (FIG. 1) or isolated platelets (FIG. 2) were incubated with or antibody SSA78, SSA401 and SSA412 separately for 60 minutes at room temperature followed by addition of 1 µg/ml collagen. For isolated platelets, experimental sample (10 µl each) was taken from the reaction mixture on to a microscope slide and covered by a micro cover glass. Platelet aggregation and the prevention of its aggregation were detected by a ZEISS Axioskop microscope. For blood plasma, regular camera can detect the results. Method-3: Detection of NKA activator endogenous SSA412 antibody prevents thrombus formation significantly in the absence of blood flow using inferior vena cava (IVC) stasis mouse model. The in vivo stasis mouse model of deep venous thrombosis (DVT) involves a total occlusion or ligation of the IVC, below the renal veins, with a non-reactive suture. Back branches are cauterized and side branches are also ligated causing complete blood stasis. A thrombus consolidates by post-ligation and yields quantifiable amounts of thrombus. This model is well established and widely used in animal DVT studies. Experimental results reveal that a 12±2 mg (n=10) of thrombus was formed in the control mouse. In contrast, only 2.8±2 mg (n=10) of a thrombus was formed under the same experimental conditions. These data provide representative evidence to demonstrate the anti-thrombosis effect of NKA activators in animal DVT study in vivo. A: Ligation of IVC causes thrombus formation in the absence (left: control) and presence (right: +Ab). All thrombus were weighted and the mean of the thrombus was compared as shown in B (p=0.001). Method-4: Detection of anti-thrombosis effect of NKA activator SSA412 on a partial flow restriction (stenosis) mouse model. IVC ligation was performed over a 30-gauge needle and then the needle was removed (Alexander Brill, et al. Blood. 2011;117: 1400-1407). The needle was placed outside the vessel so that piercing or any other injury to the IVC wall was completely avoided. This procedure decreases the vascular lumen area to approximately 10% and allows for standardized flow restriction without endothelial injury. All visible side branches (usually 1 or 2) were also ligated. After surgery, peritoneum and skin were closed by monofilament absorbable suture and 6.0 silk, respectively. Mice were euthanized after 48 hours and thrombi were developed in the IVC below the suture. The regions of ligation and thrombus formation are indicated as arrow-1 and arrow-2, respectively. Arrow-3 indicates the IVC in the presence of SSA412. A): Partial flow stenosis of IVC causes visible thrombus formation (12 mg±3, n=10) in 48 hours absence of NKA activator SSA412. B): Significant prevention/inhibition of thrombus formation was seen (1.5 mg±2, n=10) in the presence of endogenous NKA activator SSA412 antibody. C): All thrombus were weighted and the mean of the thrombus was compared as shown in C (p=0.001).

Figure 2:
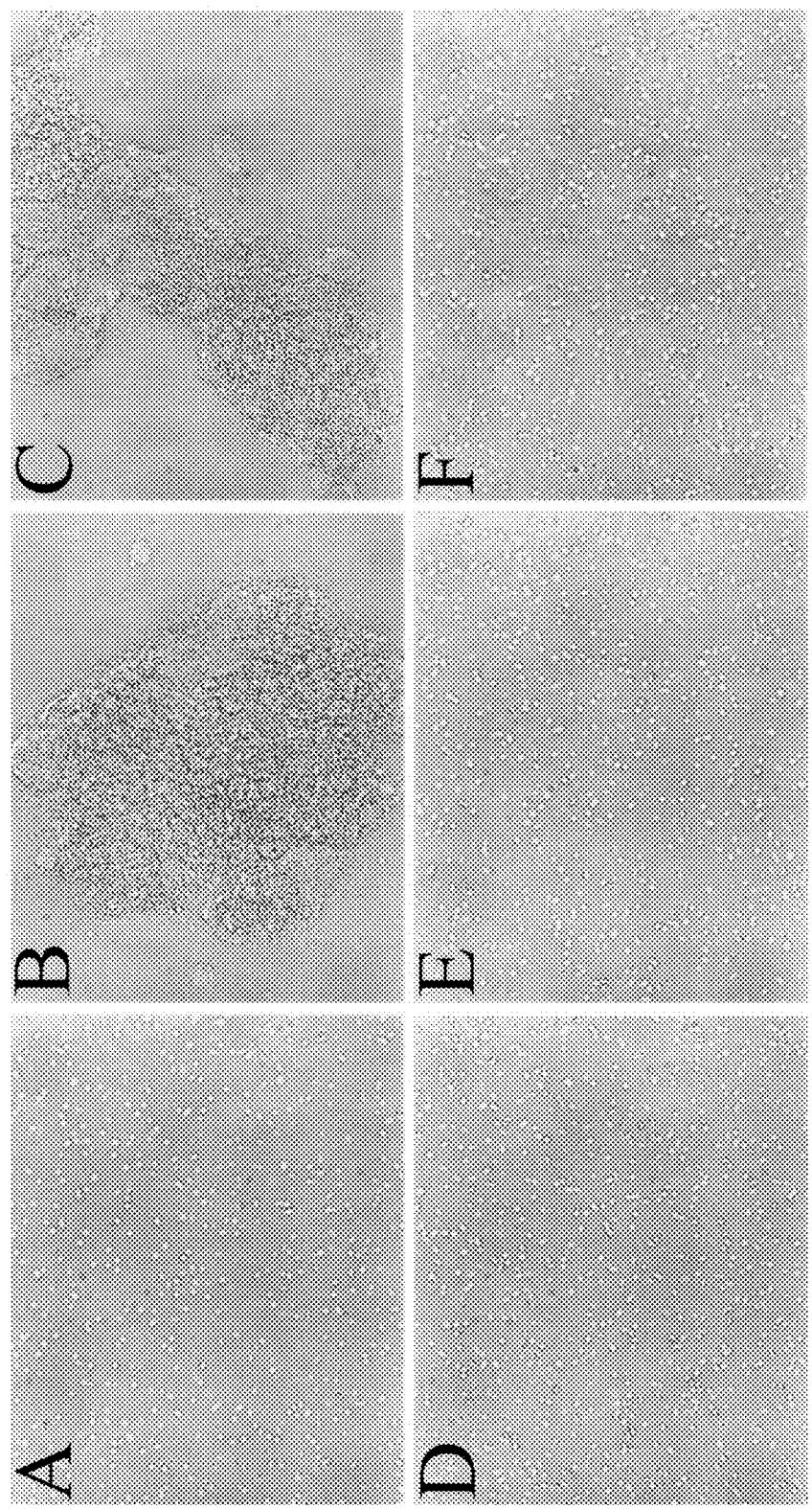
FIG. 2. NKA activator antibodies SSA78, SSA401, and SSA412 prevent collagen-induced platelet aggregation in isolated rat platelets. A): Isolated platelets; B): Condition A+1 µg/ml collagen; C): Condition B+0.2 µM total rabbit IgG; D): Condition B+0.2 µM SSA78; E): Condition B+0.2 µM SSA401; F) Condition B+0.2 µM SSA412.(400X magnification for all conditions).

As shown in FIG. 2, collagen induced activation and aggregation in an isolated rat platelets. In distinct contrast, 0.2 µM polyclonal antibodies SSA78, SSA401 and SSA412 prevented platelet activation and aggregation in the presence of collagen. Similar results were found when testing on human plasma, collagen induced platelet activation and aggregation as shown in FIG. 1 and NKA activator antibodies SSA78, SSA401, and SSA412 prevented the formation of platelet aggregation, which demonstrate that NKA activator antibodies have the capability to prevent platelet aggregation, which may be potentially used to prevent and treat thrombosis and its associated disorders, including stroke, myocardial infarction and pulmonary embolism.

Platelet Inhibition in the Presence of Collagen

Materials: Aggregometer (Chrono-Log Corporation), isotonic saline, collagen (1 mg/ml), and human blood. Method: Impedance measurement: Electrical impedance aggregation measurements were performed on an aggregometer (Chrono-Log Corporation, 560 model), which can be equipped with automated calibration and readout functions. The instrument can be maintained according to the manufacturer instructions for proper cleaning and maintenance of the electrode. The blood sample (0.5 mL each) can be incubated with or without antibody (0.2 µM) for 60 minutes at room temperature prior to be diluted with an equivalent volume of isotonic saline and incubated for 5 minutes at 37° C. The impedance of each sample can be monitored in sequential 1-minute intervals until a stable baseline can be established. After a stable baseline is established, the collagen can be added to the sample, aggregation can be monitored for approximately 8-11 minutes, and the final increase in ohms over this period can be displayed as a numeric LED readout. In addition, a graphical printout (i.e., chart tracing) of each electrical impedance aggregometry tracing can be obtained.

The experimental results can be seen in both 1 (upper curve) and 5 (lower curve) µg/ml collagen induced platelet aggregation. NKA activator antibodies and significantly inhibited platelet activation and aggregation by using Aggregometer. This method can be used to demonstrate that NKA activator antibodies have the capability to prevent platelet aggregation.

Bleeding Tests

Rats were immunized with antigen SSA78 (RSA-TEEEPPNDD; SEQ ID NO:3), antigen SSA401 (HLL-GIRETWDDRWIN; SEQ ID NO:4), and antigen SSA412 (DVEDSYGQQWTYEQR; SEQ ID NO:5) separately for one month. ELISA assay analyses demonstrated the generation of endogenous SSA78, SSA401, and SSA412 antibodies.

Figure 3:
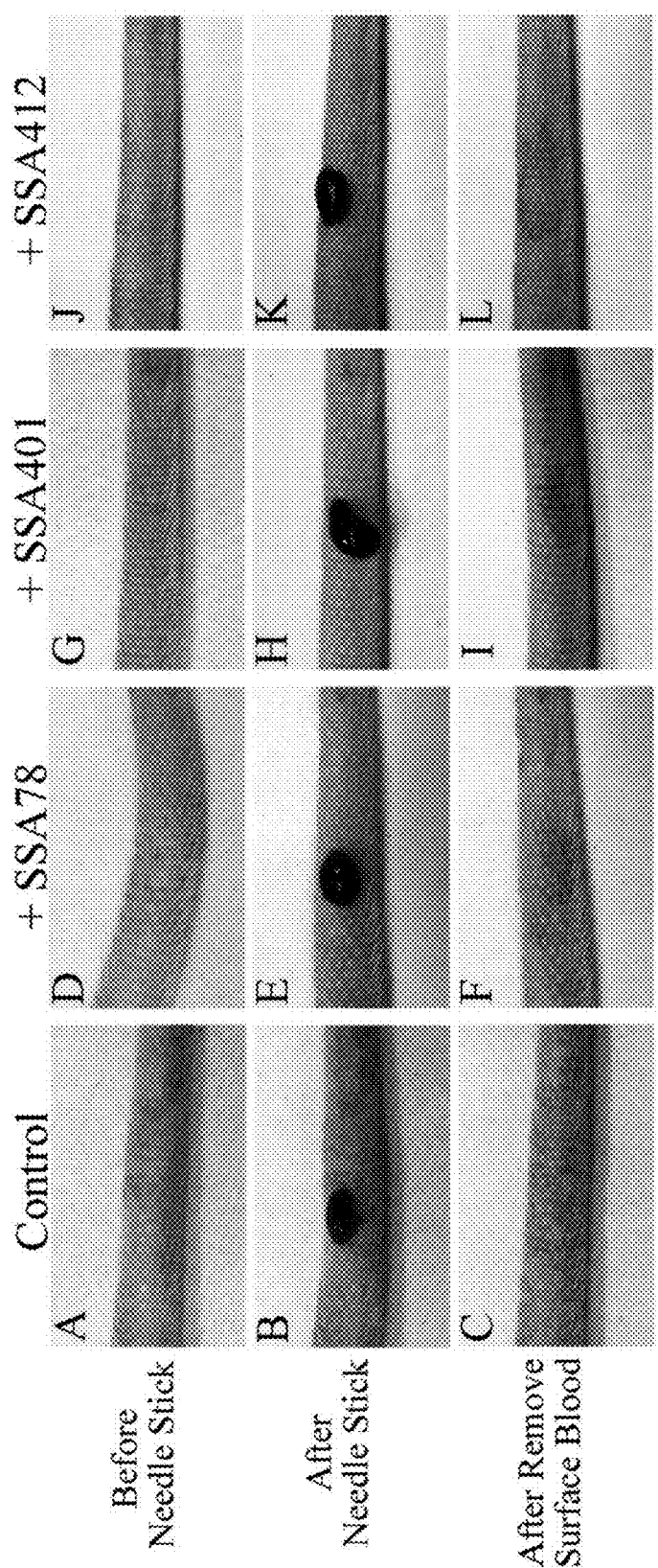
FIG. 3. Bleeding test. Rats were active immunized with or without antigens of SSA78, SSA401, and SSA412 (100 μg antigen per rat) separately. Generation of endogenous SSA78, SSA401 and SSA412 antibodies in each rat was determined by ELISA analyses following 30 days of immunization. Backgrounds of rat tails under with or without immunization conditions before the needle stick are shown as A (control without immunization), D, G, and J (with active immunizations to generate specific endogenous antibody as indicated). A quick bleeding test was performed at the rat lateral tail vein. Blood came out from lateral tail vein immediately after needle stick (B, E, H, and K). No bleeding was detected after removal of tail surface blood (C, F, I, and L). Experimental data show that NKA activator antibodies do not cause bleeding (n=5/each group).
Figure 4:
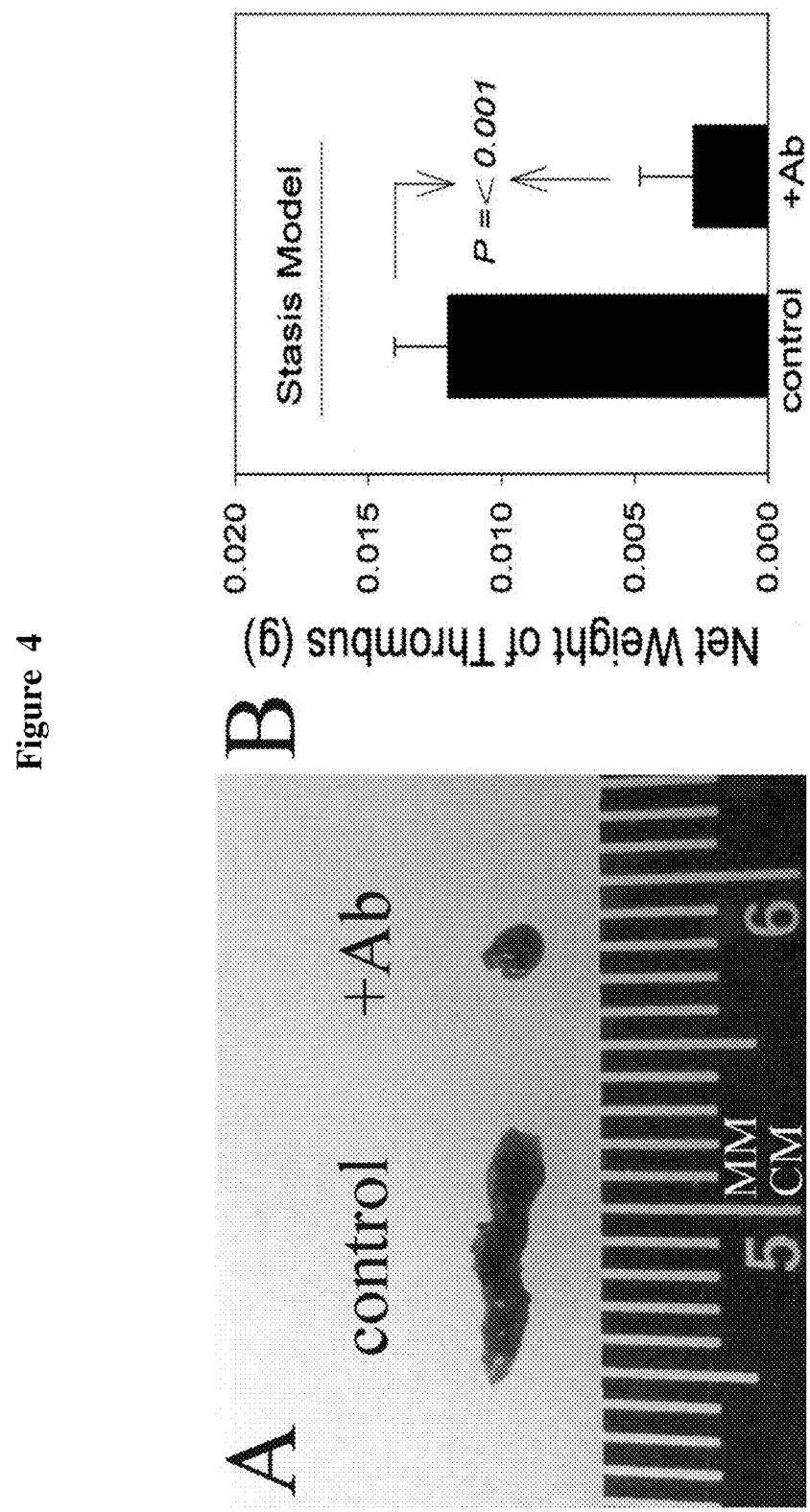
FIG. 4. Representative NKA activator endogenous SSA412 antibody prevents thrombus formation significantly in the absence of blood flow using inferior vena cava (IVC) stasis mouse model. The in vivo stasis mouse model of deep venous thrombosis (DVT) involves a total occlusion or ligation of the IVC, below the renal veins, with a non-reactive suture. Back branches are cauterized and side branches are also ligated causing complete blood stasis. A thrombus consolidates by post-ligation and yields quantifiable amounts of thrombus. This model is well established and widely used in animal DVT studies. Experimental results reveal that a 12±2 mg (n=10) of thrombus was formed in the control mouse. In contrast, only 2.8±2 mg (n=10) of a thrombus was formed under the same experimental conditions. These data provide representative evidence to demonstrate the anti-thrombosis effect of NKA activators in animal DVT study in vivo. A: Ligation of IVC causes thrombus formation in the absence (left: control) and presence (right: +Ab). All thrombus were weighted and the mean of the thrombus was compared as shown in B (p=0.001).
Figure 5:
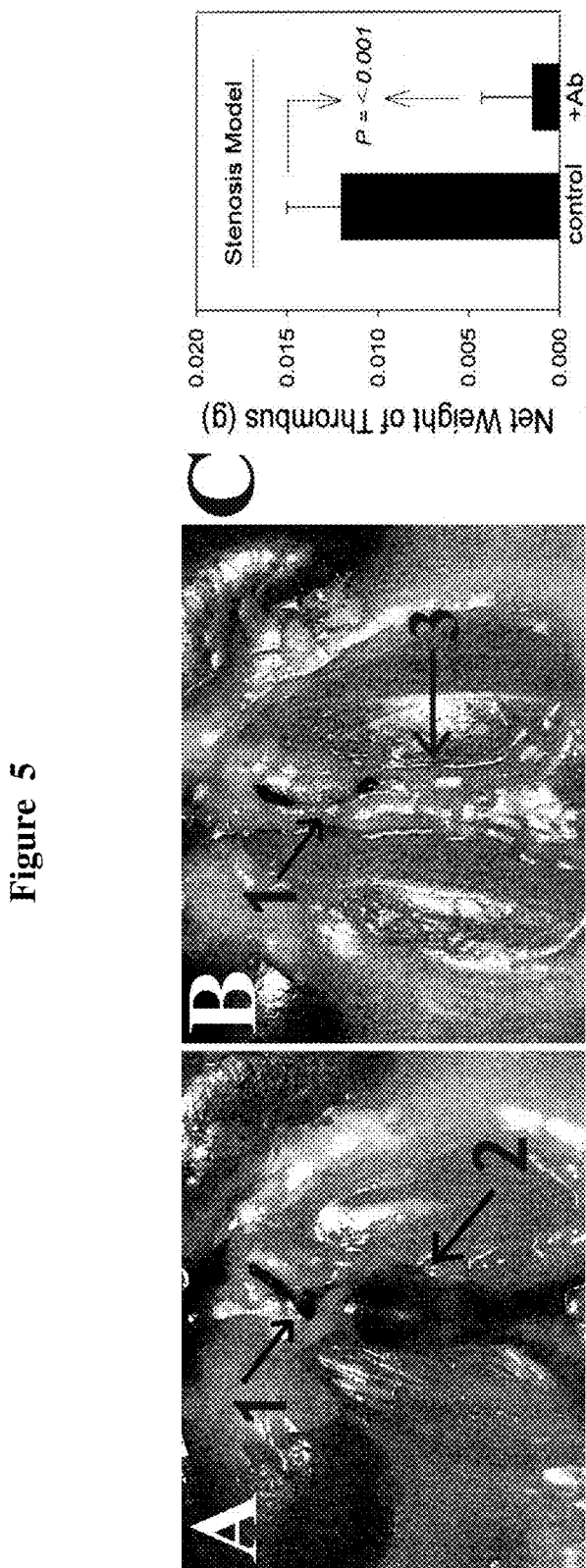
FIG. 5. Representative anti-thrombosis effect of NKA activator SSA412 on a partial flow restriction (stenosis) mouse model. IVC ligation was performed over a 30-gauge needle and then the needle was removed (Alexander Brill, et al. Blood. 2011;117: 1400-1407). The needle was placed outside the vessel so that piercing or any other injury to the IVC wall was completely avoided. This procedure decreases the vascular lumen area to approximately 10% and allows for standardized flow restriction without endothelial injury. All visible side branches (usually 1 or 2) were also ligated. After surgery, peritoneum and skin were closed by monofilament absorbable suture and 6.0 silk, respectively. Mice were euthanized after 48 hours and thrombi were developed in the IVC below the suture. The regions of ligation and thrombus formation are indicated as arrow-1 and arrow-2, respectively. Arrow-3 indicates the IVC in the presence of SSA412. A): Partial flow stenosis of IVC causes visible thrombus formation (12 mg±3, n=10) in 48 hours absence of NKA activator SSA412. B): Significant prevention/inhibition of thrombus formation was seen (1.5 mg±2, n=10) in the presence of endogenous NKA activator SSA412 antibody. C): All thrombus were weighted and the mean of the thrombus was compared as shown in C (p=0.001).

A bleeding test was performed at the rat lateral tail vein. Representative FIG. 3 has shown the control background of rat tail before needle stick (A, D, G, and J). B, E, H and K show blood from lateral tail vein after needle stick. The C, F, I and L show after removal of the blood. Time length of the bleeding test from beginning and finish was 5-6 seconds. Five Rats were used per each group and all rats had similar results. NKA activator antibodies SSA78, SSA401, and SSA412 were thus found to not increase bleeding in experimental animals.

Antibody Involvement in Conventional Drug Pathways

Table 1 illustrates that NKA activator antibodies do not participate in any of the conventional drug pathways and suggests the basis as to why NKA activator antibodies do not cause bleeding.

| Drug Name | Irreversible Binding | Inhibition of Clotting Factors | Inhibition of Forming Thrombin | Inhibition of IIB/IIIa Pathways |
| --- | --- | --- | --- | --- |
| Aspirin | Yes | | | |
| Clopidogrel | Yes | | | |
| Abciximab | Yes | | | |
| Coumarins | | Yes | | |
| Hirudin | | | Yes | |
| Argatroban | | | Yes | |
| Tirofiban | | | | Yes |
| Eptifibatide | | | | Yes |
| NKA antibody activators | No | No | No | No |

What is claimed is:

1. A method for inhibiting platelet activation and aggregation without causing bleeding in a subject comprising administering to the subject a pharmaceutical effective amount of an antibody comprising a heavy chain variable domain and a light chain variable domain that specifically binds to the amino acid sequence of SEQ ID NO: 4 of the α subunit of (Na$^+$+K$^+$)-ATPase, wherein the heavy chain variable domain comprises the amino acid sequence of SEQ ID NO: 8 and the light chain variable domain comprises the amino acid sequence of SEQ ID NO: 9, wherein the antibody comprises humanized or human versions thereof, or a fragment thereof wherein the fragment is a single-chain antibody, and optionally, wherein the fragment comprises one or more conservative amino acid substitutions.

2. The method of claim 1, wherein the antibody is selected from the group consisting of IgG1, IgG2, IgG3, IgG4, IgM, IgA1, IgA2, IgD, and IgE, wherein the antibody fragment comprises one or more conservative amino acid substitutions.

3. The method of claim 1, wherein the antibody is a polyclonal antibody or a monoclonal antibody.

4. The method of claim 1, wherein the antibody is in a pharmaceutical formulation comprising the antibody and a pharmaceutically acceptable carrier.

5. The method of claim 1, wherein the subject has or is at greater risk than the general population for thrombosis.

6. A method for inhibiting thrombosis without causing bleeding in a subject comprising administering to the subject an effective amount of an antibody comprising a heavy chain variable domain and a light chain variable domain that specifically binds to the amino acid sequence of SEQ ID NO: 4 of the α subunit of (Na$^+$+K$^+$)-ATPase, wherein the heavy chain variable domain comprises the amino acid sequence of SEQ ID NO: 8 and the light chain variable domain comprises the amino acid sequence of SEQ ID NO: 9, wherein the antibody comprises humanized or human versions thereof, or a fragment thereof wherein the fragment is a single-chain antibody, and optionally, wherein the fragment comprises one or more conservative amino acid substitutions.

7. The method of claim 6, wherein the antibody is in a pharmaceutical formulation comprising the antibody and a pharmaceutically acceptable carrier.

8. The method of claim 6, wherein the subject has or is at greater risk than the general population for thrombosis selected from the group consisting of venous thrombosis, deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, arterial thrombosis, stroke, pulmonary embolism, coronary heart disease, angina, heart failure, heart valve disease, atherosclerosis, a myocardial infarction, and post-surgical thrombotic complications arising from angioplasty and organ transplantation.

* * * * *

SEQUENCE LISTING

<160> NUMBER OF SEQ ID NOS: 9

<210> SEQ ID NO 1
<211> LENGTH: 15
<212> TYPE: PRT
<213> ORGANISM: Artificial Sequence
<220> FEATURE:
<223> OTHER INFORMATION: Activation site of the (Na+K)-ATPase

<400> SEQUENCE: 1

Lys Arg Gln Pro Arg Asn Pro Lys Thr Asp Lys Leu Val Asn Glu
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: Activation site of the (NA+K)-ATPase

<400> SEQUENCE: 2

Val Pro Ala Ser Leu Ala Tyr Glu Gln Ala Glu Ser Asp
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Activation site of the (Na+K)-ATPase

<400> SEQUENCE: 3

Arg Ser Ala Thr Glu Glu Glu Pro Pro Asn Asp Asp
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Activation site of the (Na+K)-ATPase

<400> SEQUENCE: 4

His Leu Leu Gly Ile Arg Glu Thr Trp Asp Asp Arg Trp Ile Asn
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Activation site of the (Na+K)-ATPase

<400> SEQUENCE: 5

Asp Val Glu Asp Ser Tyr Gly Gln Gln Trp Thr Tyr Glu Gln Arg
1               5                   10                  15

<210> SEQ ID NO 6
<211> LENGTH: 122
<212> TYPE: PRT
<213> ORGANISM: Artificial Sequence
<220> FEATURE:
<223> OTHER INFORMATION: Mouse monoclonal antibody

<400> SEQUENCE: 6

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Thr Ile Asn Pro His Ser Gly Ser Ser Tyr Tyr Ser Glu Lys Phe
    50                  55                  60

```
Lys Ser Lys Ala Thr Leu Thr Ala Asp Thr Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Ala Val Ala Gly Gly Tyr Tyr Asp Gln Gly Ala Leu Asp Tyr Trp
            100                 105                 110

Gly Arg Gly Thr Ser Val Thr Val Ser Ser
        115                 120

<210> SEQ ID NO 7
<211> LENGTH: 112
<212> TYPE: PRT
<213> ORGANISM: Artificial Sequence
<220> FEATURE:
<223> OTHER INFORMATION: mouse monoclonal antibody

<400> SEQUENCE: 7

Asp Ile Val Met Ser Gln Ser Pro Ser Ser Leu Ala Val Ser Ala Gly
  1               5                  10                  15

Glu Lys Val Thr Met Ser Cys Lys Ser Ser Gln Ser Leu Phe Asn Ser
                 20                  25                  30

Arg Thr Arg Lys Asn Tyr Leu Ala Trp Tyr Gln Gln Lys Pro Gly Gln
             35                  40                  45

Ser Pro Lys Leu Leu Ile Tyr Trp Ala Ser Thr Arg Glu Ser Gly Val
         50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Tyr Ser Tyr Leu Arg Thr Phe Gly Gly Gly Thr Lys Leu Glu Ile Lys
            100                 105                 110

<210> SEQ ID NO 8
<211> LENGTH: 121
<212> TYPE: PRT
<213> ORGANISM: Artificial Sequence
<220> FEATURE:
<223> OTHER INFORMATION: Mouse monoclonal antibody

<400> SEQUENCE: 8

Gln Val Gln Leu Gln Gln Pro Gly Ala Glu Val Val Lys Pro Gly Thr
  1               5                  10                  15

Ser Val Lys Leu Ser Cys Lys Ala Ser Gly Tyr Lys Phe Thr Thr Tyr
                 20                  25                  30

Trp Ile Asn Trp Leu Lys Leu Arg Pro Gly Gln Gly Lys Glu Trp Ile
             35                  40                  45

Gly Asp Phe Tyr Pro Gly Asn  Gly Ser Asn Asn Phe Asn Asp Lys Phe
         50                  55                  60

Arg  Asn Lys Lys Thr Leu Thr Val Asp Thr Ser Ser Asn Thr Ala Tyr
 65                  70                  75                  80

Met Gln Leu Ser Ser Leu Ala Ser Glu Asp  Ser Ala Leu Tyr Tyr Cys
                 85                  90                  95

Ala Arg Ser Ile Trp Ala Thr Arg Leu Trp Tyr Phe Asp Val Trp Gly
            100                 105                 110

Ala Gly Thr Thr Val Thr Val Ser Ser
        115                 120
```

```
<210> SEQ ID NO 9
<211> LENGTH: 108
<212> TYPE: PRT
<213> ORGANISM: Artificial Sequence
<220> FEATURE:
<223> OTHER INFORMATION: Mouse monoclonal antibody

<400> SEQUENCE: 9

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly  Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
            85                  90                  95

Glu Leu Thr Arg Ser Glu Gly Gly Pro  Ser Trp Lys
            100                 105
```